United States Patent [19]

Cross et al.

[11] 4,273,782

[45] Jun. 16, 1981

[54] INHIBITION OF THROMBOXANE SYNTHETASE BY 3-(1-IMIDAZOLYLALKYL) INDOLES

[75] Inventors: Peter E. Cross, Canterbury; Roger P. Dickinson, Dover, both of England

[73] Assignee: Pfizer Inc., New York, N.Y.

[21] Appl. No.: 127,298

[22] Filed: Mar. 5, 1980

[30] Foreign Application Priority Data

Mar. 7, 1979 [GB] United Kingdom ............... 08123/79

[51] Int. Cl.$^3$ .................... A61K 31/415; C07D 403/06
[52] U.S. Cl. ................................ 424/273 R; 424/250; 424/251; 424/263; 424/270; 544/238; 544/322; 544/328; 544/331; 544/405; 546/273; 548/181; 548/252; 548/254; 548/336
[58] Field of Search ............... 548/336, 254, 181, 252; 546/273; 544/405, 238, 328, 322, 331; 424/273 R, 250, 251, 263, 270

[56] References Cited

U.S. PATENT DOCUMENTS

| | | | |
|---|---|---|---|
| 3,190,889 | 6/1965 | Shen | 548/336 X |
| 3,454,586 | 7/1969 | Suh | 548/336 X |
| 3,621,027 | 11/1971 | Schoen et al. | 548/336 X |
| 3,931,229 | 1/1976 | Zinnes et al. | 548/336 X |
| 4,059,583 | 11/1977 | McComsey et al. | 548/336 X |
| 4,140,858 | 2/1979 | Zinnes et al. | 548/336 |
| 4,217,357 | 8/1980 | Cross et al. | 548/336 X |

FOREIGN PATENT DOCUMENTS

3901 9/1979 European Pat. Off. .

OTHER PUBLICATIONS

Andreani, F. et al., *J. Chem. Soc.* (C), 1970, 1157–1161.
Decodts, G. et al., *Comptes Rendus Acad. Sci. Paris*, 266, 1168–1170 (1968).

*Primary Examiner*—Richard A. Schwartz
*Attorney, Agent, or Firm*—Francis X. Murphy; Charles J. Knuth; Peter C. Richardson

[57] ABSTRACT

Novel 3-(1-Imidazolylalkyl)indoles and the pharmaceutically acceptable acid addition salts thereof are disclosed. The novel compounds are useful in selectively inhibiting the action of the thromboxane synthetase enzyme without significantly inhibiting the action of the prostacycline synthetase or cyclooxygenase enzymes and are thus of value as therapeutic agents for the treatment of ischaemic heart disease, stroke, transient ischaemic attack, thrombosis, migraine and the vascular complications of diabetes.

27 Claims, No Drawings

INHIBITION OF THROMBOXANE SYNTHETASE BY 3-(1-IMIDAZOLYLALKYL) INDOLES

BACKGROUND OF THE INVENTION

This invention relates to indole derivatives, and in particular to certain 3-(1-imidazolylalkyl)indoles. Such compounds are able to selectively inhibit the action of the thromboxane synthetase enzyme without significantly inhibiting the action of the prostacyclin synthetase or cyclo-oxygenase enzymes. The compounds may thus be useful in, for example, the treatment of thrombosis, ischaemic heart disease, stroke, transient ischaemic attack, migraine and the vascular complications of diabetes.

SUMMARY OF THE INVENTION

Thus, according to the invention there are provided compounds of the general formula:

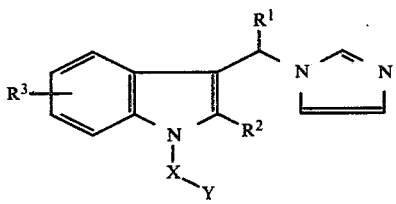

(I)

wherein
$R^1$ is hydrogen or $C_1$–$C_4$ lower alkyl;
$R^2$ is hydrogen, $C_1$–$C_6$ alkyl, $C_3$–$C_6$ cycloalkyl or a phenyl group optionally substituted with $C_1$–$C_4$ lower alkyl, $C_1$–$C_4$ lower alkoxy, fluorine, chlorine or bromine;
$R^3$ is hydrogen, $C_1$–$C_4$ lower alkyl, $C_1$–$C_4$ alkoxy, hydroxy, trifluoromethyl, di($C_1$–$C_4$ lower alkyl)amino, fluorine, chlorine or bromine;
X is a group:

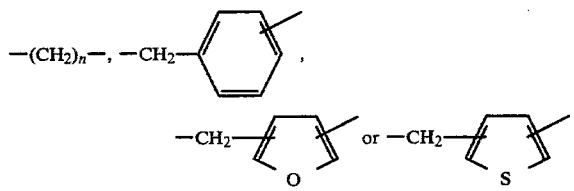

wherein n is an integer of from 1 to 3;
Y is $CO_2R^4$, $CONHR^5$, $CON(C_1$–$C_4$ lower alkyl$)_2$, CN, 5-tetrazolyl, $CONHCOR^6$, CONHCN or $CONHSO_2R^6$, or, when
X is $-(CH_2)_n-$ and n is 2 or 3,
Y is $NH_2$, $NHCOR^6$, $NHCO_2(C_1$–$C_4$ lower alkyl), $NHCONHR^5$, $NHSO_2R^6$, OH or a group:

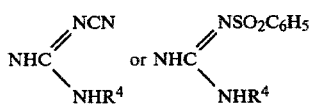

$R^4$ is hydrogen or $C_1$–$C_4$ lower alkyl;
$R^5$ is hydrogen, $C_1$–$C_4$ lower alkyl, $C_3$–$C_6$ cycloalkyl, phenyl, thiazolyl, pyridyl, pyrazinyl, pyrimidinyl, or pyridazinyl;
$R^6$ is $C_1$–$C_4$ lower alkyl, $C_3$–$C_6$ cycloalkyl, pyridyl or a phenyl group optionally substituted with $C_1$–$C_4$ lower alkyl, $C_1$–$C_4$ lower alkoxy, fluorine, chlorine or bromine;
and the pharmaceutically acceptable acid addition salts thereof and bioprecursors therefor.

The invention also provides a method of inhibiting the action of the thromboxane synthetase enzyme in an animal, including a human being, without significantly inhibiting the action of the prostacyclin synthetase or cyclo-oxygenase enzymes, which comprises administering to the animal an effective amount of a compound of the formula (I), or a pharmaceutically acceptable salt thereof, or a pharmaceutical composition comprising such a compound or salt together with a pharmaceutically acceptable diluent or carrier.

The invention further provides a compound of the formula (I), or a pharmaceutically acceptable salt thereof, or pharmaceutical composition comprising such a compound or salt together with a pharmaceutically acceptable diluent or carrier, for use in treating an animal, including a human being, to inhibit the action of the thromboxane synthetase enzyme without significantly inhibiting the action of the prostacyclin synthetase or cyclo-oxygenase enzymes.

The invention also includes a pharmaceutical composition comprising a compound of the formula (I), or a pharmaceutically acceptable salt thereof, together with a pharmaceutically acceptable diluent or carrier.

The invention also includes pharmaceutically acceptable bioprecursors of compounds of the formula (I). For the purpose of this specification the term "pharmaceutically acceptable bioprecursor" of a compound of the formula (I) means a compound having a structural formula different from the compounds of the formula (I) but which nonetheless, upon administration to an animal or human being, is converted in the patient's body to a compound of the formula (I).

Pharmaceutically acceptable acid addition salts of the compounds of the invention are salts with acids containing pharmaceutically acceptable anions, e.g. the hydrochloride, hydrobromide, sulphate or bisulphate, phosphate or acid phosphate, acetate, maleate, fumarate, lactate, tartrate, citrate, gluconate, succinate and p-toluene sulphonate salts.

Alkyl and alkoxy groups having 3 or more carbon atoms and alkanoyl groups having 4 carbon atoms may be straight or branched chain.

Preferred compounds of the invention are those in which $R^1$ is hydrogen, $R^3$ is hydrogen or bromine, and $R^2$ is hydrogen, isopropyl or cyclopropyl particularly where $R^1$, $R^2$ and $R^3$ are each hydrogen. In one preferred group of compounds X is $-(CH_2)_n-$ particularly $-CH_2-$ or $-(CH_2)_2-$. In a further preferred group of compounds X is a benzyl group, particularly a 4-substituted benzyl group.

Preferred Y groups are $CO_2H$, $CO_2CH_2CH_3$, $CONH_2$, $CONHC_6H_5$, $NHCOC_6H_5$, $NHSO_2C_6H_5$, $NHCONHCH_3$, $NHCONHC_6H_5$ and tetrazolyl; $CO_2H$ and $CONH_2$ being particularly preferred.

Particularly preferred individual compounds include:
5-Bromo-1-carboxyethyl-3-(1-imidazolylmethyl)indole,
1-carboxyethyl-3-(1-imidazolylmethyl)indole,
1-carboxyethyl-2-cyclopropyl-3-(1-imidazolylmethyl)indole,
1-(4-carboxybenzyl)-3-(1-imidazolylmethyl)indole,
1-carboxymethyl-3-(1-imidazolylmethyl)indole,
1-carbamoylethyl-3-(1-imidazolylmethyl)indole, and
1-(4-carbamoylbenzyl)-3-(1-imidazolylmethyl)indole.

DETAILED DESCRIPTION OF THE INVENTION

The compounds of the invention may be prepared by a number of different routes:

(1) In one process according to the invention the compounds of the formula (I) where $R^1$, $R^2$, $R^3$, X and Y are as previously defined may be prepared from a compound of the formula:

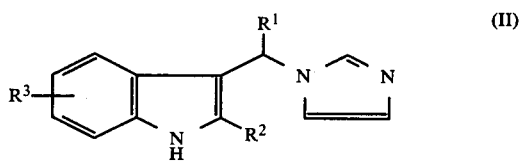
(II)

wherein $R^1$, $R^2$ and $R^3$ are as previously defined but $R^3$ may not be hydroxyl, by reacting the anion derived from (II) using a strong base with an alkylating agent of the formula:

Hal-X-Y  (III)

where Hal is chlorine, bromine or iodine, X is as previously defined and Y is $CO_2R^4$ (where $R^4$ is $C_1$-$C_4$ lower alkyl), $CONHR^5$ (where $R^5$ is $C_1$-$C_4$ lower alkyl or phenyl), $CON(C_1$-$C_4$ lower alkyl$)_2$, CN or, when X is —$(CH_2)_n$— and n is 2 or 3, $NHCOR^6$ (where $R^6$ is $C_1$-$C_4$ lower alkyl or phenyl) and optionally using conventional chemical transformation reactions to obtain those compounds of the formula (I) where Y is as previously defined other than as defined herein for the compound of formula (III), and optionally, reacting the compounds of formula (I) wherein $R^3$ is a $C_1$-$C_4$ lower alkoxy group with $BBr_3$ to give compounds where $R^3$ is hydroxyl and optionally forming a pharmaceutically acceptable salt of the product.

Suitable bases for use to generate the anion from (II) are sodamide or an alkali metal hydride; sodium hydride being a preferred base. The bromides of formula (III) where hal is bromine are preferred alkylating agents. Examples of suitable alkylating agents are esters of bromoalkanoic acids, e.g. ethyl bromoacetate, α-halotoluene derivatives, e.g. α-bromotolunitrile and ethyl α-bromotoluate, and haloalkanoylaniline derivatives, e.g. 3-chloropropionanilide.

In typical procedure the appropriate compound of the formula (II) is dissolved in a suitable solvent, e.g. dry dimethylformamide, sodium hydride is then added carefully. After formation of the anion is complete the appropriate alkylating agent is then added, and the resulting solution stirred at room temperature for up to 24 hours. The reaction mixture may then be poured into water, and the resulting mixture extracted with a suitable solvent, e.g. ethyl acetate and the organic phase washed with water, dried and evaporated to give the desired product, which if necessary may be further purified by recrystallisation or by chromatography.

The preparation of the starting materials of formula (II) is described in the specification of our European Patent Application No. 0003901 published Sept. 5, 1979.

(2) Compounds of the formula (I) where X is —$(CH_2)_2$— and Y is CN may be prepared by reaction of a compound of the formula (II) with acrylonitrile in the presence of a base. The reaction is generally performed with the compound of formula (II) and acrylonitrile dissolved in a suitable solvent e.g. dioxan. A strong organic base e.g. benzyltrimethylammonium hydroxide is then added and the resulting solution warmed, e.g. at 50°-60° C., for an hour or so. The product is isolated and further purified, if desired, as described above.

(3) Compounds of the formula (I) wherein $R^1$ to $R^3$ and X are as previously defined but $R^3$ may not be hydroxyl; and Y is $CO_2R^4$ (where $R^4$ is $C_1$-$C_4$ lower alkyl), $CONHR^5$, $CON(C_1$-$C_4$ lower alkyl$)_2$, CN, or when X is —$(CH_2)_n$— and n is 2 or 3, $NHCOR^6$, $NHCO_2(C_1$-$C_4$ lower alkyl), $NHCONHR^5$ or $NHSO_2R^6$ (wherein $R^5$ and $R^6$ are each $C_1$-$C_4$ lower alkyl or phenyl) may also be prepared from a compound of the formula:

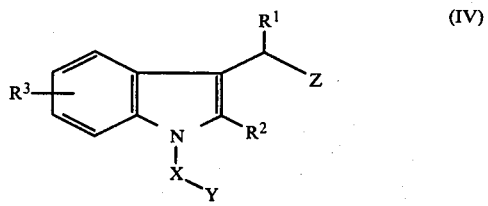
(IV)

wherein $R^1$ to $R^3$, X and Y are as defined above and Z is a good leaving group, by reacting with imidazole. Suitable leaving groups Z are —$N^\ominus(C_1$-$C_4$ lower alkyl$)_3$, —Cl, —Br, and $OSO_2(C_1$-$C_4$ lower alkyl, phenyl, tolyl or p-methoxphenyl) groups. Z is preferably a —$N^\ominus(CH_3)_3$ group.

In a typical procedure the compound of formula (IV) and imidazole are refluxed together in a suitable solvent, e.g. ethanol, for up to 6 hours. The solution is then evaporated and the product purified if desired, e.g. by chromatography and/or crystallisation.

The starting materials of formula (IV) are prepared from a compound of the formula:

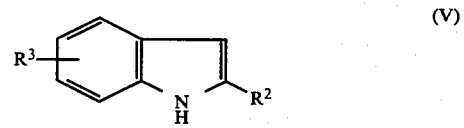
(V)

wherein $R^2$ and $R^3$ are as defined above (and $R^3$ may not be hydroxyl), by first introducing the group —X-Y by the methods as described in processes (1) or (2) above. Other methods may also be employed, for example introduction of the substituent where —X-Y is —$(CH_2)_3CO_2R^4$ may be achieved by reaction with γ butyrolactone at 200° C. (cf. Annalen, 1955, 596, 158), followed, in the case where $R^4$ is a $C_1$-$C_4$ lower alkyl group by esterification.

The imidazolylalkyl substituent as the 3-position is then introduced following the general procedure described in our European Patent Application No. 0003901 already referred to eg. by a Mannich reaction with an aldehyde $R^1CHO$ in the presence of a di-lower alkylamine e.g. dimethylamine, followed by quaternisation, e.g. with methyl iodide, to give the compound of formula (IV) wherein Z is —$N^\ominus(CH_3)_3$. The compounds of formula (V) are known compounds or are prepared by analogous methods.

(4) Compounds wherein X is a group —$(CH_2)_n$— (where n is 2 or 3) and Y is an amino group may be prepared from a compound of the formula (II) as defined above (with the proviso that $R^3$ is not hydroxyl) by alkylation with a compound of the formula:

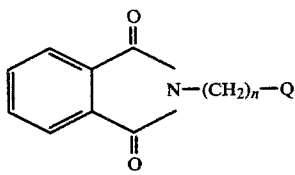

(VI)

where Q is a leaving group e.g. chloride, bromide, iodide OSO$_2$ (lower alkyl, phenyl, tolyl or p-methoxyphenyl). Iodide or methanesulphonyl are preferred leaving groups. The reaction is performed by first forming the anion of the compound of formula (II) by reaction with sodium hydride as previously described and then adding the compound of formula (VI). The reaction, which may be catalysed by the addition of sodium iodide, is generally complete within 24 hours at room temperature. The product may then be isolated by removal of the solvent and purified, if desired, prior to removal of the phthaloyl group to yield the free amine. The phthaloyl group may be removed using standard techniques for the removal of this group e.g. by heating a solution of the phthaloyl-protected product with hydrazine hydrate under reflux in ethanol for several hours, and the free amine is then isolated and purified by conventional methods.

(5) Compounds of the formula (I) wherein R$^3$ is a hydroxyl group may be obtained from the corresponding compound when R$^3$ is a C$_1$–C$_4$ lower group by reaction with boron tribromide. This reaction is performed in a conventional manner, e.g. by adding excess boron tribromide to a solution or suspension of the alkoxy-indole in an inert organic solvent e.g. dichloromethane. After several hours at room temperature methanol is added to destroy excess reagent and the hydroxy-substituted product is then isolated and purified by conventional methods as previously described.

(6) Naturally certain of the groups Y may be obtained by chemical transformation reactions and these possibilities with be well known to those skilled in the art. Thus, for example, compounds of the formula (I) wherein Y is a carboxyl group may be obtained via hydrolysis of the corresponding esters where Y is CO$_2$R$^4$ and R$^4$ is a lower alkyl group. The acid may be converted to a variety of derivatives, e.g. formation of the acid chloride or imidazolide followed by reaction with ammonia gives the amides where Y is CONH$_2$. Similarly reaction of the acid chloride or imidazolide with a C$_1$–C$_4$ lower alkylamine gives compounds where Y is CONHR$^5$ and R$^5$ is a C$_1$–C$_4$ lower alkyl group, or reaction with a di-lower alkylamine gives compounds where Y is CON(C$_1$–C$_4$ lower alkyl)$_2$ or reaction with a cycloalkylamine, aniline, or heterocyclic amine gives compounds where Y is CONHR$^5$ and R$^5$ is a cycloalkyl, phenyl or heterocyclic group.

The amides where Y is CONH$_2$ may also be prepared via hydrolysis of the compound of formula (I) where Y is a cyano group, e.g. using cold concentrated hydrochloric acid in the case of the alkyl nitriles where X is (CH$_2$)$_n$ or alkaline hydrogen peroxide in the case of the aryl nitriles where X is:

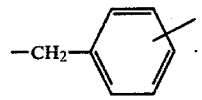

More vigorous alkaline hydrolysis of the nitrile can also be used to give the corresponding acids where Y is a carboxyl group, or alternatively, the 5-tetrazolyl ring may be built up by reaction of the nitrile with an azide, e.g. sodium azide.

Compounds where Y is a group CONHCOR$^6$, CONHSO$_2$R$^6$ or CONHCN may be obtained by treatment of the corresponding acid imidazolide with an appropriate carboxamide, sulphonamide or cyanamide at a temperature of between 100° and 150° C. In the case of compounds where Y is a group CONHSO$_2$R$^6$ or NHCN, the product is often isolated in the alternative hydroxyimino tautomeric form.

Similarly acylation or sulphonylation of a compound of the formula (I) wherein Y is an amino group with a C$_2$–C$_5$ lower alkanoyl chloride, C$_4$–C$_7$ cycloalkanoyl chloride, aroyl chloride, picoloyl chloride or C$_1$–C$_4$ lower alkyl or arylsulphonyl chloride gives the corresponding compound wherein Y is NHCOR$^6$ or NHSO$_2$R$^6$ and R$^6$ is as previously defined. Alternatively, acylation of a compound of the formula (I) wherein Y is an amino group with a C$_2$–C$_5$ lower alkanoyl, C$_4$–C$_7$ cycloalkanoyl, aroyl or picoloyl imidazolide, derived from the appropriate acid by reaction with N,N-carbonyldiimidazole, gives the corresponding compound wherein Y is NHCOR$^6$ and R$^6$ is as previously defined. Again reaction of the amine with potassium isocyanate or a C$_1$–C$_4$ lower alkyl, aryl or heterocyclic isocyanate gives compounds wherein Y is NHCONHR$^5$. The latter compounds may also be prepared by successive treatment of the amine with N,N'-carbonyldiimidazole and ammonia or an appropriate amine. Reaction of the amine with a lower alkyl chloroformate gives compounds wherein Y is NHCO$_2$(C$_1$–C$_4$ lower alkyl).

Compounds in which Y is a cyanoguanidine or arylsulphonylguanidine group may be prepared by successive treatment of a compound of the formula (I) wherein Y is an amino group with a dialkyl iminodithiocarbonate derivative of the formula (CH$_3$S)$_2$C=NCN or (CH$_3$S)$_2$C=NSO$_2$Ph followed by addition of a compound of the formula R$^4$NH$_2$.

Hydrolysis of the compounds wherein Y is NHCOR$^6$ and R$^6$ is lower alkyl or phenyl can conversely be used to prepare the compounds where Y is NH$_2$.

Compounds where Y is tetrazolyl are prepared from the cyano derivative by reaction with sodium azide and ammonium chloride.

Compounds of the formula (I) where X is (CH$_2$)$_n$, n is 2 or 3 and Y is OH may be obtained by reduction of the corresponding compound where n is 1 or 2, Y is CO$_2$R$^4$ and R$^4$ is lower alkyl, using lithium aluminium hydride.

All these reactions are entirely conventional and the methods and conditions for their performance will be well known to those skilled in the art, as with other possibilities and variations.

The pharmaceutically acceptable acid addition salts of the compounds of the invention may be prepared by conventional procedures, e.g. by reacting the free base in a suitable solvent, e.g. ethanol, with a solution containing one equivalent of the desired acid in a suitable solvent e.g. ether. The salt generally precipitates from solution or is recovered by evaporation of the solvent.

Where the compounds of the invention contain an asymmetric carbon atom the invention includes the racemic mixtures and the separated D- and L- optically active isomeric forms. Such forms should be obtainable by conventional methods, e.g. by fractional crystallisation of a salt with a suitable optically active acid, e.g. tartaric acid.

The compounds of formula (I) have been found to selectively inhibit the action of the thromboxane synthetase enzyme without significantly affecting the action of the prostacyclin synthetase or cyclooxygenase enzymes. Thus the compounds are of value in the treatment of a variety of clinical conditions which are characterised by an inbalance of prostacyclin/thromboxane $A_2$. For the reasons given below these conditions may include thrombosis, ischaemic heart disease, stroke, transient ischaemic attack, migraine and the vascular complications of diabetes.

Research work has established that in most tissues the major product of the arachidonic acid metabolism is either of two unstable substances, thromboxane $A_2$ ($TxA_2$) or prostacyclin ($PGI_2$). (Proc. Nat. Acad. Sci. U.S.A., 1975, 72, 2994, Nature, 1976, 263, 663, Prostaglandins, 1976, 12, 897). In most cases the prostaglandins $PGE_2$, $PGF_2$ and $PGD_2$ are comparatively minor by-products in this bio-synthetic pathway. The discovery of thromboxane $A_2$ and prostacyclin has significantly increased our understanding of vascular homeostasis, prostacyclin for instance is a powerful vasodilator and inhibitor of platelet aggregation, and in this last respect is the most potent endogenous substance so far discovered. The prostacyclin synthetase enzyme is located in the endothelial layer of the vasculature, and is fed by endoperoxides released by blood platelets coming into contact with the vessel wall. The prostacyclin thus produced is important for prevention of platelet deposition on vessel walls. (Prostaglandins, 1976, 12, 685, Science, 1976, 17, Nature, 1978, 273, 765).

Thromboxane $A_2$ is synthesised by the thromboxane synthetase enzyme which is located in, for example, the blood platelets. Thromboxane $A_2$ is a powerful vasoconstrictor and pro-aggregatory substance. As such its actions are in direct opposition to those of prostacyclin. If, for any reason, prostacyclin formation by the vasculature is impaired, then the endoperoxides produced by platelets coming into contact with the vessel wall are converted into thromboxane, but are not converted effectively into prostacyclin (Lancet, 1977, 18, Prostaglandins, 1978, 13, 3). Alteration of the prostacyclin/-thromboxane balance in favour of the latter substance could result in platelet aggregation, vasospasm (Lancet, 1977, 479, Science, 1976, 1135, Amer. J. Cardiology, 1978, 41, 787) and an increased susceptibility to athero-thrombosis (Lancet (i) 1977, 1216). It is also known that in experimental atherosclerosis prostacyclin generation is suppressed and thromboxane $A_2$ production is enhanced (Prostaglandins, 1977, 14, 1025 and 1035). Thus thromboxane $A_2$ has been implicated as the causative agent in variant angina, myocardial infarction, sudden cardiac death and stroke (Thromb. Haemostasis, 1977, 38, 132). Studies in rabbits have shown that ECG changes typical of these conditions were produced when freshly prepared thromboxane $A_2$ was injected directly into the animal's heart (Biochem. aspects of Prostaglandins and Thromboxanes, Editors, N. Kharasch and J. Fried, Academic Press 1977 page 189). This technique is considered to represent a unique animal model of the heart attacks of coronary patients and has been used to show that administration of a compound believed to antagonise the effects of thromboxane $A_2$ protects the rabbits from the adverse consequences of thromboxane $A_2$ injection.

Another area where a $PGI_2/TxA_2$ imbalance is considered to be a contributory factor is that of migraine. The migraine headache is associated with changes in intra and extracerebral blood flow, in particular a pre-headache reduction of cerebral blood flow followed by dilatation in both vascular areas during the headache phase.

Prior to the development of the headache, blood levels of 5-hydroxytryptamine are elevated, and this suggests the occurrence of in vivo aggregation and release of the amine from the platelet stores. It is known that the blood platelets of migraine patients are more prone to aggregate than are those of normal individuals (J. Clin. Pathol., 1971, 24, 250, J. Headache, 1977, 17, 101). Furthermore, it has now been postulated that not only is an adnormality of platelet function a major factor in the pathogenesis of migraine attacks but it is in fact their prime cause (Lancet (i), 1978, 501). Thus a drug that selectively modifies platelet function to inhibit thromboxane $A_2$ formation could be of considerable benefit in migraine therapy.

Abnormalities of platelet behaviour have been reported in patients with diabetes mellitus (Metabolism, 1979, 28, 394, Lancet, 1978 (i) 235). Diabetic patients are known to be particularly susceptible to microvascular complications, atherosclerosis and thrombosis and platelet hyper-reactivity has been suggested as the cause of such angiopathy. Diabetic platelets produce elevated amounts of $TxB_2$ and malondialdehyde (Symposium "Diabetes and Thrombosis—Implications for Therapy", Leeds U.K., April 1979). Also it has been shown that in rats with experimental diabetes vascular prostacyclin production is impaired and $TxA_2$ synthesis from the platelets is elevated (IV International Prostaglandin Conference, Washington, D.C. May 1979). Thus the imbalance between prostacyclin and $TxA_2$ is considered to be responsible for the microvascular complications of diabetes. A $TxA_2$-synthetase inhibitor could therefore find clinical utility in preventing these vascular complications.

Aspirin and most other non-steroidal anti-inflammatory drugs inhibit the cyclo-oxygenase enzyme. The effect of this is to shut down the production of the $PGG_2/H_2$ endoperoxides and by so doing to reduce both the prostacyclin and thromboxane $A_2$ levels. Aspirin and aspirin-like drugs have been evaluated clinically for prevention of stroke and heart attack (New England and J. Med. 1978, 299, 53, B.M.J., 1978, 1188, Stroke, 1977, 8 301).

Although some encouraging results have been obtained with these drugs, a compound which specifically inhibits thromboxane $A_2$ formation leaving the biosynthesis of prostacyclin unimpaired would be more valuable in these clinical conditions (Lancet (ii), 1978, 780).

The effect of the compounds of the formula (I) on the thromboxane synthetase enzyme, and the prostacyclin synthetase and cyclooxygenase enzymes has been measured by the following in vitro enzyme assays:

1. Cyclo-oxygenase

Ram seminal vesicle microsomes (Biochemistry, 1971, 10, 2372) are incubated with arachidonic acid (100 $\mu$M: 1 min.: 22°) to produce $PGH_2$ and aliquots of the reaction mixture injected into a stream of Krebs-bicarbonate at 37° C. (containing a mixture of antagonists (Nature, 1978, 218, 1135) and indomethacin (Brit. J. Pharmacol., 1972, 45 451) which is superfusing a spirally-cut rabbit aorta strip (Nature, 1969, 223, 29). The ability of a compound to inhibit the enzyme is measured by comparing the increases in isometric tension produced by $PGH_2$ in the absence of the test compound, and following pre-incubation of the enzyme with the test compound for 5 minutes.

2. Prostacyclin ($PGI_2$) Synthetase

Pig aorta microsomes (Nature, 1976, 263, 663) are incubated (30 sec.: 22° C.) with $PGH_2$ produced as in 1) and aliquots bio-assayed as in 1. $PGI_2$ production is assessed indirectly by measuring the decrease in $PGH_2$-induced tension ($PGI_2$ itself does not contract the aorta). This decrease can be prevented completely by pre-incubation of the enzyme with the selective $PGI_2$ synthetase inhibitor, 15-hydroxy-arachidonic acid (Prostaglandins, 1976, 12, 715). The test compound is then pre-incubated with the enzyme for 5 minutes, and its ability to prevent the decrease in tension is measured.

3. Thromboxane $A_2$ ($TxA_2$) Synthetase

Indomethacin pre-treated human platelet microsomes (Science, 1976, 193, 163) are incubated (2 min.: 0° C.) with $PGH_2$ (produced as in 1) and aliquots of the reaction mixture superfused over two rabbit aorta spirals which are separated by a delay coil (2 min.). The latter is required to allow the selective decay of the more unstable thromboxane $A_2$ (Proc. Nat. Acad. Sci., 1975, 72, 2994) thereby enabling the separate measurement of increased isometric tension due to the $TxA_2$ formed and the $PGH_2$ remaining. The test compound is pre-incubated with enzyme for 5 minutes, and its ability to inhibit the thromboxane synthetase enzyme is measured as its reduction of the $TxA_2$ component of the isometric tension.

Compounds of the invention tested in this way have been shown to be capable of selectively inhibiting the thromboxane synthetase enzyme.

In addition to the above an in vitro assay for measuring the inhibition of human blood platelet aggregation has been described and this may be predictive of anti-thrombotic efficacy clinically (Lancet (ii), 1974, 1223, J. Exp. Med., 1967, 126, 171). Both clinically effective agents aspirin and sulphinpyrazone show inhibitory activity in vitro against a variety of aggregating agents in this test.

A number of in vivo tests in animals have also been described for evaluating potential anti-thrombotic drugs. Intravenous injection of arachidonic acid causes death in rabbits by causing platelet clumping and embolisation in the lungs. Again both the clinically effective aspirin (Agents and Actions, 1977, 1, 481) and sulphinpyrazone (Pharmacology, 1976, 14, 522) protect the rabbit from the lethal effect of the injection. Sulphinpyrazone has also been shown to prevent the aggregation of platelets in an extra corporeal loop of the abdominal aorta of rats in vivo (Thromb. Diathes. Haem., 1973, 30, 138).

The compounds may be administered orally in the form of tablets or capsules containing a unit dose of the compound together with such excipients as maize starch, calcium carbonate, dicalcium phosphate, alginic acid, lactose, magnesium stearate, "Primogel" (Trade Mark) or talc. The tablets are typically prepared by granulating the ingredients together and compressing the resulting mixture to give tablets of the desired size.

Capsules are typically prepared by granulating the ingredients together and filling them into hard gelatine capsules of the appropriate size to contain the desired dosage.

The compounds may also be administered parenterally, for example by intramuscular, intravenous or subcutaneous injection. For parenteral administration, they are best used in the form of a sterile aqueous solution which may contain other solutes such as tonic and pH adjusters. The compounds may be added to distilled water and the pH adjusted to 3-6 using an acid such as citric, lactic or hydrochloric acid. Sufficient solutes such as dextrose or saline may be added to render the solution isotonic. The resulting solution may then be sterilised and filled into sterile glass vials of an appropriate size to contain the desired volume of solution. The compounds of the invention may also be administered by the infusion of a parenteral formulation as described above into a vein.

For oral administration to human patients, it is expected that the daily dosage level of a compound of the invention will be from 0.1 to 20 mg/kg per day for a typical adult patient (70 kg). For parenteral administration, it is expected that the daily dosage level of a compound of the formula (I) will be from 0.01-0.5 mg/kg per day, for a typical adult patient. Thus tablets or capsules can generally be expected to contain from 5 to 150 mg of the active compound for administration orally up to 3 times a day. Dosage units for parenteral administration can be expected to contain from 0.5-35 mg of the active compound. A typical vial could be a 10 ml vial containing 5 mg of the active compound in 6-10 ml of solution.

It should of course be appreciated that in any event the physician will determine the actual dosage which will be most suitable for the individual and it will vary with the age, weight and response of the patient. The above dosages are exemplary of the average patient, there may of course be individual cases where higher or lower dosage ranges are merited.

Compounds of the invention tested using the methods previously described have been shown to be capable of selectively inhibiting the thromboxane snthetase enzyme. The results of these tests are shown in the following Table, which gives the molar concentration of each compound which caused a 50% change in the effect of the relevant enzyme on isometric tension, i.e. caused a 50% inhibition of the action of that enzyme.

| Example | Molar concentration causing 50% inhibition of | |
|---|---|---|
| | (1) thromboxane synthetase | (3) prostacyclin synthetase |
| 1 | $1.8 \times 10^{-8}$ | $2.4 \times 10^{-5}$ |
| 4 | $4.8 \times 10^{-9}$ | $2.2 \times 10^{-6}$ |
| 7 | $1.6 \times 10^{-10}$ | $> 10^{-4}$ |
| 10 | $1.2 \times 10^{-8}$ | $> 10^{-4}$ |
| 11 | $4.0 \times 10^{-11}$ | $> 10^{-4}$ |
| 13 | $2.0 \times 10^{-9}$ | $1.0 \times 10^{-4}$ |
| 14 | $3.7 \times 10^{-11}$ | $4.0 \times 10^{-5}$ |
| 20 | $1.8 \times 10^{-12}$ | $> 10^{-4}$ |
| 23 | $8.0 \times 10^{-10}$ | $> 10^{-4}$ |
| 24 | $1.6 \times 10^{-10}$ | $> 10^{-4}$ |
| 25 | $2.4 \times 10^{-9}$ | $> 10^{-4}$ |
| 27 | $1.4 \times 10^{-7}$ | $1.0 \times 10^{-4}$ |
| 28 | $6.0 \times 10^{-9}$ | $7.0 \times 10^{-5}$ |
| 38 | $1.3 \times 10^{-7}$ | — |
| 42 | $3.4 \times 10^{-11}$ | $4.5 \times 10^{-5}$ |
| 46 | $2.1 \times 10^{-9}$ | — |
| 47 | $5.5 \times 10^{-9}$ | $4.0 \times 10^{-5}$ |

-continued

| Example | Molar concentration causing 50% inhibition of | |
|---|---|---|
| | (1) thromboxane synthetase | (3) prostacyclin synthetase |
| 48 | $1.0 \times 10^{-9}$ | $1.0 \times 10^{-4}$ |

The results given in the Table show that all of the compounds tested caused a 50% inhibition of the thromboxane synthetase enzyme at a molar concentration of $1.0 \times 10^{-7}$ or less, and several caused 50% inhibition at concentrations of $10^{-10}$ or less.

Of the compounds tested for inhibition of the prostacyclin synthetase enzyme none caused 50% inhibition at a molar concentration less than 450 times greater than that at which they caused 50% inhibition of the thromboxane synthetase enzyme, i.e. they were all at least 450 times more potent as inhibitors of thromboxane synthetase than of prostacyclin synthetase and many were more potent by a considerably greater factor.

It is expected that all the compounds of the invention when tested in this way will give results within the range of those already tested.

The preparation of the novel compounds of the invention is illustrated by the following Examples:

EXAMPLE 1

1-(2-Cyanoethyl)-3-(1-imidazolylmethyl)indole fumarate

A 40% solution of benzyltrimethylammonium hydroxide in methanol (0.5 ml) was added to a suspension of 3-(1-imidazolylmethyl) indole (1.97 g) in dioxan (25 ml) containing acrylonitrile (2.0 ml) to give a clear solution. The solution was heated to 50°–60° C. for 30 minutes and then allowed to cool and stand overnight at room temperature. It was then poured into water and the mixture was extracted with ethyl acetate (3×50 ml). The combined extracts were washed with water and dried ($Na_2SO_4$). Evaporation of the solvent gave 1-cyanoethyl-3-(1-imidazolylmethyl)indole (2.50 g) as an oil.

The oil was dissolved in a few ml of ethanol and a slight excess of a saturated solution of fumaric acid in ether was added. the precipitate was filtered off and crystallised from 2-butanone/petrol (b.p. 60°–80° C.) to give 1-(2-cyanoethyl)-3-(1-imidazolylmethyl)indole fumarate, m.p. 167°–169° C. Analysis %: Found: C, 61.93; H, 4.99; N, 15.14. $C_{15}H_{14}N_4.C_4H_4O_4$ requires: C, 62.28; H, 4.95; N, 15.29.

EXAMPLE 2

1-(2-Cyanoethyl)-3-[1-(1-imidazolyl)ethyl]indole fumarate

Treatment of 3-[1-(1-imidazolyl)ethyl]indole with acrylonitrile according to the method of Example 1 gave an oil which was purified by chromatography on silica gel. Elution with chloroform gave the product as an oil. A portion was treated with fumaric acid as described in Example 1 and the resulting solid was crystallised from ethyl acetate to give 1-(2-cyanoethyl)-3-[1-(1-imidazolyl)ethyl]indole fumarate, m.p. 128°–129° C. Found: C, 62.80; H, 5.33; N, 14.48. $C_{16}H_{16}N_4.C_4H_4O_4$ requires: C, 63.15; H, 5.30; N, 14.73%.

EXAMPLE 3

1-(2-Cyanoethyl)-3-(1-imidazolylmethyl)-5-methoxyindole

Treatment of 3-(1-imidazolylmethyl)-5-methoxyindole with acrylonitrile and purification of the crude product as described in Example 2 gave 1-(2-cyanoethyl)-3-(1-imidazolylmethyl)-5-methoxyindole, m.p. 130° C. (from chloroform/petrol) (b.p. 60°–80° C.). Found: C, 68.22; H, 5.72; N, 19.99. $C_{16}H_{16}N_4O$ requires: C, 68.55; H, 5.72; N, 19.99%.

Other 1-(2-cyanoethyl)indole analogues have been prepared in a similar manner from the appropriate 3-(1-imidazolylmethyl)indoles. In all cases the crude product was partially purified by chromatography on silica gel using chloroform as eluent and was used without further characterisation as starting materials for Examples 12–22 and 28–37.

The preparation of the 3-(1-imidazolylmethyl)indole starting materials is described in European Patent Application No. 0003901 with the exception of 5-chloro-3-(1-imidazolylmethyl)indole which was prepared as follows:

A solution of 5-chlorogramine (3.73 g) and imidazole (1.22 g) in xylene (20 ml) was heated under reflux for 3 hours and the cooled. The solid was filtered off, washed with toluene followed by petrol and then crystallised from a mixture of isopropanol and petrol (b.p. 60°–80° C.) to give 5-chloro-3-(1-imidazolylmethyl)indole (3.50 g), m.p. 195°–197° C. Found: C, 62.48; H, 4.31; N, 18.09. $C_{12}H_{10}ClN_3$ requires: C, 62.20; H, 4.35; N, 18.14%.

EXAMPLE 4

1-(4-Cyanobenzyl)-3-(1-imidazolylmethyl)indole 3-(1-Imidazolylmethyl)indole (4.93 g) was dissolved in dry N,N-dimethylformamide (25 ml) and the solution was cooled to 0° C. Sodium hydride (1.2 g of 50% dispersion in oil) was added portionwise with stirring and the mixture was stirred at 0° C. for 30 minutes. A solution of α-bromo-p-tolunitrile (4.90 g) in dry N,N-dimethylformamide (10 ml) was added with stirring over 2 minutes and the mixture was stirred at room temperature for 2 hours and then poured into water. The mixture was extracted with ethyl acetate (3×50 ml) and the combined extracts were washed with water and dried ($Na_2SO_4$). Evaporation of the solvent gave an oil which was chromatographed on silica gel. The column was first eluted with a mixture of chloroform and petrol (b.p. 60°–80° C.) (1:1) to remove some impurity and mineral oil, and pure product was then eluted using a mixture of chloroform and methanol (95:5). Evaporation of the eluate gave an oil (7.25 g) which crystallised on standing. The solid was recrystallised from ethyl acetate/petrol (b.p. 60°–80° C.) to give 1-(4-cyanobenzyl)-3-(1-imidazolylmethyl)indole, m.p. 127°–129° C. Found: C, 76.55; H, 5.15; N, 17.80. $C_{20}H_{16}N_4$ requires: C, 76.90; H, 5.16; N, 17.94%.

EXAMPLE 5

1-(2-Cyanobenzyl)-3-(1-imidazolylmethyl)indole

This compound was prepared as described in Example 4 using α-bromo-o-tolunitrile instead of α-bromo-p-tolunitrile. The product had m.p. 135°–136.5° C. (from ethyl acetate/petrol (b.p. 60°–80° C.)).

Found: C, 77.10; H, 5.22; N, 17.92. $C_{20}H_{16}N_4$ requires: C, 76.90; H, 5.16; N, 17.94%.

EXAMPLE 6

1-(3-Cyanobenzyl)-3-(1-imidazolylmethyl)indole fumarate

This compound was prepared as described in Example 4 using α-bromo-m-tolunitrile instead of α-bromo-p-tolunitrile. The fumarate salt had m.p. 156°–158° C. (from isopropanol/petrol b.p. 60°–80° C.).

Found: C, 67.01; H, 4.70; N, 12.95. $C_{20}H_{16}N_4.C_4H_4O_4$ requires: C, 67.28; H, 4.71; N, 13.08%.

EXAMPLE 7

1-(4-Ethoxycarbonylbenzyl)-3-(1-imidazolylmethyl)indole hemi-fumarate

This compound was prepared as described in Example 4 using ethyl (α-bromo-p-toluate) instead of α-bromo-p-tolunitrile. The hemifumarate salt had m.p. 120°–122° C. (from isopropanol/petrol b.p. 60°–80° C.). Found: C, 68.61; H, 5.37; N, 9.76. $C_{22}H_{21}N_3O_2.\frac{1}{2}C_4H_4O_4$ requires: C, 69.05; H, 5.55; N, 10.07%.

EXAMPLE 8

1-(4-Ethoxycarbonylbenzyl)-3-(1-imidazolylmethyl)-5-methoxyindole

This compound was prepared as described in Example 4 using 3-(1-imidazolylmethyl)-5-methoxyindole and ethyl (α-bromo-p-toluate) as starting materials. The fumarate salt hemihydrate had m.p. 113°–114° C. Found: N, $C_{23}H_{23}N_3O_3.C_4H_4O_4.\frac{1}{2}H_2O$ requires: C, 63.02; H, 5.48; N, 8.16%.

EXAMPLE 9

1-(3-Ethoxycarbonylpropyl)-3-(1-imidazolylmethyl)indole fumarate (i) Phosphorus oxychloride (10 ml) was added dropwise with cooling to a stirred solution of 1-(3-carboxypropyl)indole (100 g) in ethanol (750 ml). The solution was heated under reflux for 8 hours and then evaporated. The residue was distilled to give 1-(3-ethoxycarbonylpropyl)indole (95.0 g), b.p. 164°–170° C./2 m.m.

(ii) Dimethylamine hydrochloride (8.5 g) was dissolved in 40% aqueous formaldehyde solution (7.9 g) and the resulting solution was added dropwise with stirring to 1-(3-ethoxycarbonylpropyl)indole (23.1 g) at such a rate that the temperature did not exceed 35° C. The mixture was stirred at room temperature for 3 hours and then poured into a solution of sodium hydroxide (4.5 g) in water (50 ml). The mixture was extracted with ethyl acetate (3×150 ml) and the combined organic layers were washed with water and dried ($Na_2SO_4$). Evaporation of the solvent gave an oil which was fractionally distilled. The fraction boiling at 162°–170°/0.1 m.m. was collected to give 1-(3-ethoxycarbonylpropyl)-3-dimethyl-aminoethylindole (2.8 g).

(iii) Methyl iodide (1.70 g) was added to a solution of 1-(3-ethoxycarbonylpropyl)-3-dimethylaminomethylindole (2.80 g) in dry ether (100 ml). The mixture was allowed to stand at 0° C. for 18 hours and filtered to give 3-[1-(3-ethoxycarbonylpropyl)indolylmethyl]-trimethylammonium iodide (4.30 g), m.p. 154°–156° C. Found: C, 50.10; H, 6.36; N, 6.57. $C_{18}H_{27}IN_2O_2$ requires: C, 50.46; H, 6.35; N, 6.54%.

(iv) A solution of 3-[1-(3-ethoxycarbonylpropyl)indolylmethyl]trimethylammonium iodide (3.30 g) and imidazole (0.53 g) in ethanol (50 ml) was heated under reflux for 6 hours. The solution was filtered and evaporated and the residue was chromatographed on silica gel. Elution with chloroform gave first some impurity followed by pure product. Evaporation of the product containing fractions gave an oil (0.35 g) which was dissolved in ether and treated with a slight excess of an ethereal solution of fumaric acid. The solid product was filtered off and crystallised from a mixture of ethanol and ether to give 1-(3-ethoxycarbonylpropyl)-3-(1-imidazolylmethyl)indole fumarate (0.20 g), m.p. 116°–118° C. Found: C, 61.58; H, 5.92; N, 9.81. $C_{18}H_{21}N_3O_2.C_4H_4O_4$ requires: C, 61.81; H, 5.90; N, 9.83%.

EXAMPLE 10

1-Ethoxycarbonylmethyl-3-(1-imidazolylmethyl)indole

This compound was prepared as described in Example 4 using ethyl bromoacetate instead of α-bromo-p-tolunitrile. The product had m.p. 123°–124° C. (from ethyl acetate/petrol (b.p. 60°–80° C.)). Found: C, 67.51; H, 6.03; N, 14.68. $C_{16}H_{17}N_3O_2$ requires: C, 67.82; N, 6.05; N, 14.83.

EXAMPLE 11

1-(2-Carboxyethyl)-3-(1-imidazolylmethyl)indole fumarate monohydrate

A mixture of 1-(2-cyanoethyl-3-(1-imidazolyl methyl)-indole (1.0 g) and 10% aqueous potassium hydroxide (10 ml) was heated under reflux for 2 hours to give a clear solution. The solution was just acidified with acetic acid and then evaporated. The residue was chromatographed on silica gel. Elution with a mixture of chloroform and methanol (1:1) gave first a small amount of impurity followed by pure product. Evaporation of the product-containing eluate gave an oil which was dissolved in the minimum volume of ethanol. A slight excess of a saturated ethanolic solution of fumaric acid was added and the mixture was diluted with ether. The precipitate was collected by filtration and crystallised from methanol to give 1-(2-carboxyethyl)-3-(1-imidazolylmethyl)indole fumarate monohydrate 0.45 g, m.p. 161°–163° C.

Found: C, 56.67; H, 4.82; N, 9.97. $C_{15}H_{15}N_3O_2.C_4H_4O_4.H_2O$ requires: C, 56.57; H, 5.25; N, 10.42.

EXAMPLES 12–22

Other 1-(2-carboxyethyl)indole analogues prepared in a similar manner from the appropriate 1-(2-cyanoethyl)indoles are listed in Table 1. In some cases the crude product crystallised out after acidification and chromatography was not necessary. Example 20 was purified by dissolving in aqueous sodium hydroxide, filtering and reprecipitating the product with acetic acid.

TABLE I $$R^3 \text{—indole with } R^1 \text{ at 3-CH, } R^2 \text{ at 2-position, N-CH}_2\text{CH}_2\text{CO}_2\text{H, and imidazolylmethyl group}$$

| Example | R¹ | R² | R³ | M.P. (°C.) | Recrystallisation Solvent | Analysis % C | H | N (Theoretical in brackets) |
|---|---|---|---|---|---|---|---|---|
| 12 | H | CH₃ | H | 195–197 | Methanol/Ethyl Acetate | 68.22 (67.82 | 6.07 6.05 | 14.96 14.83) |
| 13 | H | CH(CH₃)₂ | H | 200–202 | H₂O | 69.43 (69.49 | 6.80 6.85 | 13.50 13.47) |
| 14 | H | cyclopropyl | H | 156–158 | Methanol/Ether | 69.60 (69.88 | 6.30 6.9 | 13.35 13.58) |
| 15 | H | p-tolyl (—C₆H₄—CH₃) | H | 176–178 | Ethanol/H₂O | 73.52 (73.51 | 5.83 5.89 | 11.75 11.69) |
| 16 | H | CH₃ | H | 196–197 | Ethanol | 68.22 (67.82 | 6.07 6.05 | 14.96 14.83) |
| 17 | H | H | 5-CH₃ | 178–179 | Ethanol | 67.72 (67.82 | 5.98 6.05 | 14.66 14.83) |
| 18 | H | H | 5-OCH₃ | 189–190 | Ethanol | 63.90 (64.20 | 5.79 5.72 | 13.74 14.04) |
| 19 | H | H | 5-Cl | 188–189 | Ethanol | 58.78 (59.31 | 4.73 4.65 | 13.62 13.84) |
| 20 | H | H | 5-Br | 195–197 | — | 51.50 (51.74 | 4.07 4.05 | 12.00 12.07) |
| 21 | H | H | 5-N(CH₃)₂ | 158–159 | Ethyl Acetate/Petrol (bp.40–68) | 64.65 (65.36 | 6.33 6.45 | 17.98 17.94) |
| 22 | H | H | 6-CF₃ | 186–187 | Ethanol | 56.06 (56.30 | 4.00 4.13 | 12.27 12.31) |

EXAMPLE 23

1-Carboxymethyl-3-(1-imidazolylmethyl)indole

1-Ethoxycarbonylmethyl-3-(1-imidazolylmethyl)indole (0.98 g) was dissolved in ethanol (10 ml) and a solution of sodium hydroxide (0.25 g) in water (2 ml) was added. The mixture was heated under reflux for 2 hours and then evaporated. The residue was dissolved in 5 ml of water and the solution was just acidified with acetic acid. The solution was evaporated to dryness and the residue was stirred with a little water and the mixture was filtered to give 1-carboxymethyl-3-(1-imidazolylmethyl)indole, (0.65 g), m.p. 218°–220° C., raised to 223°–224° C. on crystallisation from water. Found: C, 65.47; H, 5.11; N, 16.19. $C_{14}H_{13}N_3O_2$ requires: C, 65.87; H, 5.13; N, 16.46.

EXAMPLE 24

1-(4-Carboxybenzyl)-3-(1-imidazolylmethyl)indole 1-(4-Ethoxycarbonylbenzyl)-3-(1-imidazolylmethyl)indole (1.53 g) was dissolved in ethanol (25 ml) and a solution of sodium hydroxide (0.2 g) in water (5 ml) was added. The solution was heated under reflux for 2 hours and then evaporated. The residue was taken up in water and the solution was just acidified with acetic acid. A gummy precipitate was formed which solidified on scratching. The solid was filtered off, washed with water and crystallised from ethanol to give 1-(4-carboxybenzyl)-3-(1-imidazolylmethyl)indole (0.76 g), m.p. 234°–235° C. Found: C, 72.32; H, 4.96; N, 12.67. $C_{20}H_{17}N_3O_2$ requires: C, 72.49; H, 5.17; N, 12.68.

EXAMPLE 25

1-(3-Carboxybenzyl)-3-(1-imidazolylmethyl)indole 1-(3-Cyanobenzyl)-3-(1-imidazolylmethyl)indole (1.0 g) was dissolved in ethanol (5 ml) and a solution of potassium hydroxide (0.5 g) in water (5 ml) was added. The mixture was heated under reflux for 6 hours and then worked up, as described in Example 11, to give 1-(3-carboxybenzyl)-3-(1-imidazolylmethyl)indole (0.70 g), m.p. 201.5°–203.5° C. (from ethanol). Found: C, 72.16; H, 5.19; N, 12.66. $C_{20}H_{17}N_3O_2$ requires: C, 72.49; H, 5.17; N, 12.68.

EXAMPLE 26

1-(4-Carboxybenzyl)-3-(1-imidazolylmethyl)-5-methoxy-indole

This compound was prepared as described in Example 24 using 1-(4-ethoxycarbonylbenzyl)-3-(1-imidazolylmethyl)-5-methoxy-indole as starting material. The crude product was purified by dissolving in the minimum volume of N sodium hydroxide solution, filtering and reprecipitating with acetic acid. The pure product had m.p. 232°–3° C. Found: C, 69.79; H, 5.30; N, 11.63. $C_{21}H_{19}N_3O_3$ requires: C, 69.41; H, 5.43; N, 11.36%.

EXAMPLE 27

1-Carbamoylmethyl-3-(1-imidazolylmethyl)indole

Concentrated ammonium hydroxide (10 ml, S.G. 0.880) was added to a solution of 1-ethoxycarbonylmethyl-3-(1-imidazolylmethyl) indole (0.50 g) in ethanol (5 ml) and the mixture was stirred at room temperature for 2 hours. The solid was filtered off, washed with water, dried and crystallised from ethanol/petrol (b.p. 60°–80° C.) to give 1-carbamoylmethyl-3-(1-imidazolylmethyl)indole (0.24 g), m.p. 211°–212° C. Found: C, 65.65; H, 5.58; N, 21.69. $C_{14}H_{14}N_4O$ requires: C, 66.12; H, 5.55; N, 22.04.

EXAMPLE 28

1-(2-Carbamoylethyl)-2-isopropyl-3-(1-imidazolylmethyl)indole 1-(2-Cyanoethyl)-2-isopropyl-3-(1-imidazolylmethyl)indole (2.0 g) was dissolved in concentrated hydrochloric acid (10 ml) and the solution was allowed to stand for 18 hours at room temperature. It was cautiously basified with dilute sodium hydroxide solution and the mixture was extracted with ethyl acetate (3×25 ml). The combined ethyl acetate extracts were washed with water and dried ($Na_2SO_4$). The solvent was evaporated and the residue was chromatographed on silica gel. Elution with a mixture of chloroform and methanol (95:5) gave initially a small amount of impurity followed by pure product. Evaporation of the product containing fraction gave a gum which solidified on trituration with ethanol. The solid was crystallised from ethanol/petrol (b.p. 60°–80° C.) to give 1-(2-carbamoylethyl)-2-isopropyl-3-(1-imidazolylmethyl)indole (1.03 g), m.p. 169°–171° C. Found: C, 69.54; H, 7.25; N, 18.12. $C_{18}H_{22}N_4O_4$ requires: C, 69.64; H, 7.14; N, 18.05.

EXAMPLES 29–37

Other 1-(2-carbamoylethyl)indole analogues prepared from the appropriate 1-(2-cyanoethyl)indoles as described in Example 28 are listed in Table 2.

EXAMPLE 38

1-(4-Carbamoylbenzyl)-3-(1-imidazolylmethyl)indole 1-(4-Cyanobenzyl)-3-(1-imidazolylmethyl)indole (1.0 g) was dissolved in ethanol (10 ml) and 30% hydrogen peroxide (5 ml) and 6 N sodium hydroxide (5 ml) were added. The resulting mixture was stirred for 2 hours at 50° C. and then poured into water. The solid product was filtered off, washed with water and crystallised from ethanol to give 1-(4-carbamoylbenzyl)-3-(1-imidazolylmethyl)indole (0.65 g), m.p. 173°–175° C. Found: C, 72.63; H, 5.54; N, 16.29: $C_{20}H_{18}N_4O_4$ requires: C, 72.71; H, 5.49; N, 16.96.

EXAMPLE 39

1-[2-(N-Ethylcarbamoyl)ethyl]-3-(1-imidazolylmethyl)indole

Oxalyl chloride (0.50 g) was added dropwise to a solution of 1-(2-carboxyethyl)-3-(1-imidazolylmethyl)indole (1.0 g) in dry chloroform (10 ml). The mixture was stirred at room temperature for 1 hour and then warmed on a steam bath for 10 minutes and evaporated to dryness. The residual oil was redissolved in dry chloroform (5 ml) and ethylamine (5 ml) in dry chloroform (5 ml) was added and the mixture was stirred at room temperature for 2 hours and then evaporated. 2 N Sodium hydroxide was added and the mixture was extracted with methylene chloride (3×25 ml). The combined extracts were washed with water, dried ($MgSO_4$) and evaporated to give a solid which was crystallised from petrol (b.p. 60°–80° C.) to give 1-[2-(N-ethylcarbamoyl)ethyl]-3-(1-imidazolylmethyl)indole (0.25 g), m.p. 128° C. Found: C, 68.89; H, 6.73; N, 18.63. $C_{17}H_{20}N_4O$ requires: C, 68.89; H, 6.80; N, 18.91.

TABLE II

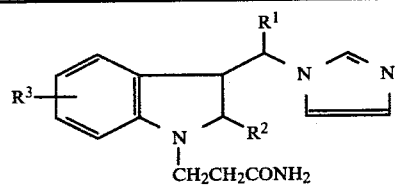

$CH_2CH_2CONH_2$

| Example | $R^1$ | $R^2$ | $R^3$ | M.P. (°C.) | Recrystallisation Solvent | Analysis % (Theoretical in brackets) | | |
|---|---|---|---|---|---|---|---|---|
| | | | | | | C | H | N |
| 29 | H | H | H | 109–112 | Methanol/$H_2O$ | 62.57 (62.92) | 6.23 6.34 | 19.68 19.57)* |
| 30 | H | $C_6H_5$ | H | 182–184 | Isopropanol/Petrol (b.p. 60–80°) | 73.27 (73.23) | 6.01 5.86 | 15.89 16.27) |
| 31 | $CH_3$ | H | H | 99–103 | $H_2O$ | 63.97 (63.98) | 6.70 6.71 | 18.49 18.66)* |
| 32 | H | H | $CH_3$ | 128–132 | Ethanol/$H_2O$ | 64.38 (63.98) | 6.63 6.71 | 18.85 18.66)* |
| 33 | H | H | 5-$OCH_3$ | 135–136 | Ethyl Acetate + Trace of Methanol | 64.30 (64.41) | 6.06 6.08 | 18.89 18.78) |
| 34 | H | H | 5-Cl | 120–122 | Ethanol | 56.51 (56.16) | 5.46 5.18 | 17.71 17.47) |
| 35 | H | H | 5-Br | 113–115 | Ethanol/$H_2O$ | 51.32 (51.88) | 4.79 4.35 | 15.84 16.14) |
| 36 | H | H | 5-$N(CH_3)_2$ | 150–151 | Ethyl Acetate/petrol (b.p. 40–60°) | 65.18 (65.57) | 6.72 6.80 | 22.42 22.49) |
| 37 | H | H | 6-$CF_3$ | 227.5–229 | Ethyl Acetate/Ether | 56.50 (57.14) | 4.50 4.50 | 16.17 16.66) |

*Monohydrate

EXAMPLE 40

1-[2-(N,N-Diethylcarbamoyl)ethyl]-3-(1-imidazolylmethyl)indole fumarate

Successive treatment of 1-(2-carboxyethyl)-3-(1-imidazolylmethyl)indole with oxalyl chloride and then dimethylamine according to the method of Example 39 gave an oil which was chromatographed on silica gel. Elution with chloroform gave an oil which was dissolved in ether and treated with an excess of an ethereal solution of fumaric acid. The solid product was collected and crystallised from a mixture of isopropanol and ethyl acetate to give 1-[2-(N,N-diethylcarbamoyl)ethyl]-3-(1-imidazolylmethyl)indole fumarate, m.p. 124° C. Found: C, 62.55; H, 6.26; N, 12.62. $C_{19}H_{24}N_4O.C_4H_4O_4$ requires: C, 62.71; H, 6.41; N, 12.72%.

EXAMPLE 41

1-[2-(N-Phenylcarbamoyl)ethyl]-3-(1-imidazolylmethyl)indole 3-(1-Imidazolylmethyl)indole (1.97 g) was dissolved in dry N,N-dimethylformamide (50 ml) and the solution was cooled to °C. Sodium hydride (0.55 g of 50% dispersion in oil) was added portionwise with stirring and the mixture was stirred at 0° C. for 30 minutes. A solution of 3-chloropropionanilide (1.83 g) in dry N,N-dimethylformamide was added dropwise with stirring and the resulting mixture was stirred at 0° C. for 2 hours followed by 18 hours at room temperature. The mixture was evaporated and water was added to the residue. The solid product was filtered off, washed with chloroform to remove impurity and crystallised from methanol to give 1-[2-(N-phenylcarbamoyl)ethyl]-3-(1-imidazolylmethyl)indole (1.20 g), m.p. 254°–255° C. Found: C, 73.14; H, 5.82; N, 15.88. $C_{21}H_{20}N_4O$ requires: C, 73.23; H, 5.85; N, 16.27%.

EXAMPLE 42

1-[2-(5-Tetrazolyl)ethyl]-3-(1-imidazolylmethyl)indole

A mixture of 1-cyanoethyl-3-(1-imidazolylmethyl)indole (2.50 g), sodium azide (3.25 g) and ammonium chloride (2.67 g) in N,N-dimethylformamide (25 ml) was heated on a steam bath for 18 hours and then evaporated to dryness. Water was added and the mixture was extracted with chloroform (2×50 ml). The combined chloroform extracts were dried (Na2SO4) and evaporated to give a gum which was chromatographed on silica gel. Elution with a mixture of chloroform and methanol (15:1) gave initially some impurity followed by pure product. Evaporation of the product containing fraction gave a gum which crystallised on standing. The solid was re-crystallised from ethyl acetate containing a trace of methanol to give 1-[2-(5-tetrazolyl)ethyl]-3-(1-imidazolylmethyl)indole (0.45 g), m.p. 180°–181° C. Found: C, 61.43; H, 5.25; N, 33.59. $C_{15}H_{15}N_7$ requires: C, 61.42; H, 5.15; N, 33.43.

EXAMPLE 43

1-[4-(5-Tetrazolyl)benzyl]-3-(1-imidazolylmethyl)indole

Treatment of 1-(4-cyanobenzyl)-3-(1-imidazolylmethyl)indole with sodium azide and ammonium chloride according to the method of Example 42 gave 1-4-(5-tetrazolyl)benzyl-3-(1-imidazolylmethyl)indole, m.p. 187°–188° C. (from ethanol/ethyl acetate). Found: C, 67.27; H, 4.66; N, 27.53. $C_{20}H_{17}N_7$ requires: C, 67.59; H, 4.82; N, 27.58%.

EXAMPLE 44

1-(2-Hydroxyethyl)-3-(1-imidazolylmethyl)indole

A suspension of 1-ethoxycarbonylmethyl-3-(1-imidazolylmethyl)indole (1.42 g) in dry tetrahydrofuran (30 ml) was added portionwise to a stirred suspension of lithium aluminium hydride (0.19 g) in dry nitrogen. The mixture was heated under reflux with stirring for 6 hours, and then cooled and a further 0.19 g of lithium aluminium hydride was added. The mixture was heated under reflux with stirring for a further period of 3 hours and then cooled. Water (0.4 ml) was added cautiously with stirring and cooling followed by 5 N sodium hydroxide solution (0.4 ml) and a further 1.2 ml of water. The mixture was filtered and the filtrate was evaporated. The residue was chromatographed on silica gel, eluting with a mixture of chloroform and methanol (20:1) to give a solid. Crystallisation from ethyl acetate/petrol (b.p. 60°–80° C.) gave 1-(2-hydroxyethyl)-3-(1-imidazolylmethyl)indole, (0.55 g), m.p. 134°–135° C. Found: C, 69.75; H, 6.25; N, 17.46. $C_{14}H_{15}N_3O$ requires: C, 69.69; H, 6.27; N, 17.42%.

EXAMPLE 45

1-(3-Aminopropyl)-3-(1-imidazolylmethyl)indole (i) 3-(1-Imidazolylmethyl)indole (3.94 g) was dissolved in N,N-dimethylformamide (50 ml) and the solution was treated with sodium hydride (1.00 g of 50% dispersion in oil) as described in Example 44. To the solution of the anion at 0° C. was added sodium iodide (3.0 g) and N-(3-bromopropyl)phthalimide (5.36 g) over 10 minutes. The mixture was then stirred at room temperature for 20 hours and evaporated to dryness. The residue was chromatographed on silica gel. The column was first eluted with petrol (b.p. 40°–60° C.) to remove mineral oil and then with chloroform to remove the product. The chloroform eluate was evaporated to give a viscous gum which was pure enough for further reaction. A portion was dissolved in ethyl acetate and the solution was treated with an excess of fumaric acid in ethyl acetate. The solid was filtered off and crystallised from ethyl acetate containing a trace of ethanol to give 1-(3-phthalimidopropyl)-3-(1-imidazolylmethyl)indole fumarate, m.p. 166°–167° C. Found: C, 64.56; H, 4.78; N, 11.09. $C_{23}H_{20}N_4O_2.C_4H_4O_4$ requires: C, 64.79; H, 4.83; N, 11.20.

(ii) A solution of the product from the first stage (1.15 g) and hydrazine hydrate (0.17 g) in ethanol (30 ml) was heated under reflux for 3 hours. The resulting mixture was cooled and filtered The filtrate was evaporated and the residue was taken up in chloroform and the mixture was filtered. The filtrate was evaporated to give 1-(3-aminopropyl)-3-(1-imidazolylmethyl)indole as an oil which was used directly without further purification in the following Examples 46 to 48.

EXAMPLE 46

N-Methyl-N'-[3-[3-(imidazol-1-ylmethyl)indol-1-yl]propyl]urea

Methyl isocyanate (0.29 g) was added dropwise to a solution of 1-(3-aminopropyl)-3-(1-imidazolylmethyl)indole (1.27 g) in chloroform (25 ml) and the solution was heated under reflux for 2.5 hours. The solution was evaporated to dryness and the residue was chromatographed on silica gel. The column was eluted first with chloroform to remove impurity and then with a mixture of chloroform and methanol (20:1). Evaporation of the product containing fractions gave a gum which crystallised on standing. The solid was recrystallised from ethyl acetate containing a trace of methanol to give N-methyl-N'-[3-[3-(imidazol-1-ylmethyl)indol-1-yl]propyl]urea (0.48 g), m.p. 123°–124° C. Found: C, 66.17; H, 7.00; N, 22.62. $C_{17}H_{21}N_5O$ requires: C, 65.57; H, 6.50; N, 22.49.

EXAMPLE 47

N-Phenyl-N'-[3-[3-(imidazol-1-ylmethyl)indol-1-yl]propyl]urea

Treatment of 1-(3-aminopropyl)-3-(1-imidazolylmethyl)indole with phenyl isocyanate as described in Example 46 gave N-phenyl-N'-[3[3-(imidazol-1-ylmethyl)indol-1-yl]propyl]urea, m.p. 177°–178° C. (from ethyl acetate containing a trace of methanol). Found: C, 70.36; H, 6.12; N, 18.76. $C_{22}H_{23}N_5O$ requires: C, 70.75; H, 6.21; N, 18.76.

EXAMPLE 48

1-(3-Benzenesulphonylaminopropyl)-3-(1-imidazolylmethyl)indole

A mixture of 1-(3-aminopropyl)-3-(1-imidazolylmethyl)indole (1.27 g) and benzenesulphonyl chloride (0.88 g) in pyridine (15 ml) was heated on a steam bath for 2 hours and then evaporated to dryness. The residue was treated with an aqueous solution of sodium bicarbonate and the mixture was extracted with ethyl acetate (2×50 ml). The combined extracts were washed with water and dried ($Na_2SO_4$). The solvent was evaporated and the residue was chromatographed on silica gel. The column was first eluted with chloroform to remove a small amount of impurity and then the product was eluted with a mixture of chloroform and methanol (20:1). Evaporation of the product containing fractions gave an oil which crystallised on standing. The product was recrystallised from ethyl acetate containing a trace of methanol to give 1-(3-benzenesulphonylaminopropyl)-3-(1-imidazolylmethyl)indole (0.58 g), m.p. 130°–131° C. Found: C, 63.71; H, 5.58; N, 14.03. $C_{21}H_{22}N_4O_2S$ requires: C, 63.93; H, 5.62; N, 14.20.

EXAMPLE 49

1-(2-Aminoethyl)-3-(1-imidazolylmethyl)indole (i) Successive treatment of 3-(1-imidazolylmethyl)indole with sodium hydride and 2-(4-toluenesulphonyloxy)ethylphthalimide by the method of Example 45 gave a product which was chromatographed on silica gel. Elution with a mixture of chloroform and methanol (20:1) gave pure 1-(2-phthalimidoethyl)-3-(1-imidazolylmethyl)indole, m.p. 167°–168° C. (from ethanol).

(ii) Treatment of the product from the first stage with hydrazine in ethanol according to the method of Example 45 (ii) gave 1-(2-aminoethyl)-3-(1-imidazolylmethyl)indole as an oil which was used directly without further purification in the following Examples 50 to 63.

EXAMPLE 50

N-Methyl-N'-{2-[3-(imidazol-1-ylmethyl)indol-1-yl]ethyl}urea monohydrate

Treatment of 1-(2-aminoethyl)-3-(1-imidazolylmethyl)indole with methyl isocyanate by the method of Example 46 gave a solid which was purified by crystallisation from ethyl acetate to give N-methyl-N'-{2-[3-(imidazol-1-ylmethyl)indol-1-yl]ethyl}urea monohydrate, m.p. 85°–86° C. Found: C, 60.85; H, 6.63; N, 22.26. $C_{16}H_{19}N_5O H_2O$ requires: C, 60.93; H, 6.71; N, 22.21%.

EXAMPLE 51

N-Phenyl-N'-{2-[3-(imidazol-1-ylmethyl)indol-1-yl]ethyl}urea

Treatment of 1-(2-aminoethyl)-3-(1-imidazolylmethyl)indole with phenyl isocyanate as described in Example 46 gave a solid which was purified by crystallisation from ethyl acetate containing a trace of methanol to give N-phenyl-N'-{2-[3-(imidazol-1-ylmethyl)indol-1-yl] ethyl}urea, m.p. 198°–199° C. Found: C, 69.91; H, 6.01; N, 19.74. $C_{21}H_{21}N_5O$ requires: C, 70.17; H, 5.89; N, 19.49%.

EXAMPLE 52

N-{2-[3-(imidazol-1-ylmethyl)indol-1-yl]ethyl}urea

A solution of potassium cyanate (0.20 g) in water (0.5 ml) was added dropwise to a stirred solution of 1-(2-aminoethyl)-3-(1-imidazolylmethyl)indole (0.48 g) in 1 N hydrochloric acid (2.0 ml) at room temperature. The resulting solution was stirred at room temperature for 30 minutes and then basified by the addition of solid sodium bicarbonate. A gum was formed which crystallised on standing. The solid was filtered off, washed with water, dried and crystallised from a mixture of ethyl acetate and petrol (b.p. 60°–80° C.) to give N-{2-[3-(imidazol-1-ylmethyl)indol-1-yl]ethyl}urea (0.29 g), m.p. 153°–154° C. Found: C, 63.44; H, 6.10; N, 24.39. $C_{15}H_{17}N_5O$ requires: C, 63.58; H, 6.05; N, 24.72%.

EXAMPLE 53

1-(2-Benzenesulphonylaminoethyl)-3-(1-imidazolylmethyl)indole

Treatment of 1-(2-aminoethyl)-3-(1-imidazolylmethyl)indole with benzenesulphonyl chloride in pyridine according to the method of Example 48 gave 1-(2-benzenesulphonylaminoethyl)-3-(1-imidazolylmethyl) indole, m.p. 166°–167° C. (from ethyl acetate). Found: C, 62.94; H, 5.33; N, 14.38. $C_{20}H_{20}N_4O_2S$ requires: C, 63.13; H, 5.30; N, 14.73%.

EXAMPLE 54

1-(2-Benzoylaminoethyl)-3-(1-imidazolylmethyl)indole

Treatment of 1-(2-aminoethyl)-3-(1-imidazolylmethyl)indole with benzoyl chloride in pyridine according to the method of Example 48 gave 1-(2-benzoylaminoethyl)-3-(1-imidazolylmethyl)indole, m.p. 245°–246° C. (from methanol). Found: C, 73.44; H, 6.00; N, 15.92. $C_{21}H_{20}N_4O$ requires: C, 73.23; H, 5.85; N, 16.27%.

EXAMPLE 55

1-(2-Acetylaminoethyl)-3-(1-imidazolylmethyl)indole

Acetic anhydride (0.20 g) was added dropwise to a stirred solution of 1-(2-aminoethyl)-3-(1-imidazolylmethyl)indole (0.48 g) in dry chloroform (10 ml) at room temperature. The solution was stirred for 10 minutes and then evaporated. The residue was stirred with aqueous sodium bicarbonate solution and the solid product was filtered off, washed with water, dried and crystallised from ethyl acetate/petrol (b.p. 60°–80° C.) to give 1-(2-acetylaminoethyl)-3-(1-imidazolylmethyl)indole (0.26 g), m.p. 126°–128° C. Found: C, 68.08; H, 6.43; N, 20.17. $C_{16}H_{18}N_4O$ requires: C, 68.06; H, 6.43; N, 19.85%.

EXAMPLE 56

1-(2-Methoxycarbonylaminoethyl)-3-(1-imidazolylmethyl)indole

Ethyl chloroformate (0.19 g) was added dropwise to a stirred solution of 1-(2-aminoethyl)-3-(1-imidazolylmethyl)indole (0.48 g) in pyridine (5 ml) at room temperature. The solution was stirred at room temperature for 3 hours and then evaporated. The residue was stirred with aqueous sodium bicarbonate solution and the solid product was filtered off, washed with water, dried and crystallised from ethyl acetate/petrol (b.p. 60°–80° C.) to give 1-(2-methoxycarbonylaminoethyl)3-(1-imidazolylmethyl)indole (0.32 g), m.p. 78°–79° C. Found: C, 62.22; H, 5.99; N, 17.72. $C_{16}H_{18}N_4O_2.\frac{1}{2}H_2O$ requires: C, 62.52; H, 6.23; N, 18.23%.

EXAMPLE 57

N-Cyano-N'-methyl-N''-{2-[3-(imidazol-1-ylmethyl)indol-1-yl] ethyl}guanidine

Dimethylcyanodithioimidocarbonate (0.30 g) was added to a solution of 1-(2-aminoethyl)-3-(1-imidazolylmethyl)indole (0.48 g) in isopropanol (15 ml). The solution was heated under reflux for 30 minutes and then cooled. The solid was filtered off and dissolved in ethanol (30 ml). To this solution was added a solution of methylamine in ethanol (10 ml of 33% solution) and the solution was heated under reflux for 3 hours. It was then evaporated and the residue was crystallised from ethyl acetate/petrol (b.p. 60°–80° C.) to give N-cyano-N'-methyl-N''-{2-[3-(imidazol-1-ylmethyl)indol-1-yl]ethyl} guanidine (0.43 g), m.p. 172°–173° C. Found: C, 63.88; H, 6.12; N, 30.16. $C_{17}H_{19}N_7$ requires: C, 63.52; H, 5.96; N, 30.51%.

EXAMPLE 58

N-Benzenesulphonyl-N'-methyl-N''-{2-[3-(imidazol-1-ylmethyl)indol-1-yl]ethyl}guanidine N-Benzenesulphonyliminodithiocarbonic acid dimethyl ester (0.522 g) was added to a solution of 1-(3-aminoethyl)-3-(1-imidazolylmethyl)indole (0.48 g) in isopropanol (10 ml) and the solution was heated under reflux for 2 hours. A solution of 33% methylamine in ethanol (10 ml) was added and the solution was heated under reflux for a further 5 hours and then evaporated. The residue was chromatographed on silica gel. Elution with chloroform gave a small amount of impurity and the product was recovered with a mixture of chloroform and methanol (50:1). The product containing fractions were evaporated to give a gum which crystallised on standing. Recrystallisation from ethyl acetate/petrol (b.p. 60°–80° C.) gave N-benzenesulphonyl-N'-methyl-N''-{2-[3-(imidazol-1-ylmethyl)indol-1-yl]ethyl}guanidine (0.42 g), m.p. 111°–112° C. Found: C, 60.33; H, 5.50; N, 19.39. $C_{22}H_{24}N_6O_2S$ requires: C, 60.53; H, 5.54; N, 19.25%.

EXAMPLE 59

1-[2-(2-Picolinoylamino)ethyl]-3-(1-imidazolylmethyl)indole

A mixture of 2-picolinic acid (0.25 g) and N,N'-carbonyldiimidazole (0.33 g) was heated on a steam bath for 30 minutes in dioxan (10 ml) to give a clear solution. 1-(2-Aminoethyl)-3-(1-imidazolylmethyl) indole (0.48 g) in dioxan (2 ml) was added and the solution was heated on a steam bath for 1 hour and then evaporated. The residue was dissolved in ethyl acetate and the solution was washed with water and dried (NaSO$_4$). Evaporation of the solvent gave a solid which was chromatographed on silica gel. Elution with chloroform gave some impurity and pure product was eluted with a mixture of chloroform and methanol (20:1). Evaporation of the product containing fractions gave a solid which was crystallised from isopropanol/petrol to give 1-[2-(2-picolinoylamino) ethyl]-3-(1-imidazolylmethyl)indole (0.2 g), m.p. 183°–184° C. Found: C, 69.67; H, 5.6; N, 19.42. $C_{20}H_{19}N_5O$ requires: C, 69.54; H, 5.55; N, 20.28%.

EXAMPLE 60

1-[2-(4-Methylbenzoylamino)ethyl]-3-(1-imidazolylmethyl)indole

Successive treatment of p-toluic acid with N,N-carbonyldiimidazole and 1-(2-aminoethyl)-3-(1-imidazolylmethyl)indole according to the method of Example 59 gave 1-[2-(4-methylbenzoylamino)ethyl]3-(1-imidazolylmethyl)indole, m.p. 155°–156° C. (from isopropanol/petrol - b.p. 60°–80° C.). Found: C, 73.51; H, 6.19; N, 15.50. $C_{22}H_{22}N_4O$ requires: C, 73.72; H, 6.19; N, 15.63%.

EXAMPLE 61

1-[2-(4-Chlorobenzoylamino)ethyl]-3-(1-imidazolylmethyl)indole

Successive treatment of 4-chlorobenzoic acid with N,N'-carbonyl-diimidazole and 1-(2-aminoethyl)-3-(1-imidazolylmethyl)indole according to the method of Example 59 gave 1-[2-(4-chlorobenzoylamino) ethyl]-3-(1-imidazolylmethyl)indole, m.p. 149°–151° C. (from ethyl acetate/petrol (b.p. 60°–80° ). Found: C, 66.02; H, 5.09; N, 14.57. $C_{21}H_{19}ClN_4O$ requires: C, 66.57; H, 5.06; N, 14.79%.

EXAMPLE 62

1-(2-Cyclopropylcarbonylaminoethyl)-3-(1-imidazolylmethyl)indole

Successive treatment of cyclopropanecarboxylic acid with N,N'-carbonyldiimidazole and 1-(2-aminoethyl)-3-(1-imidazolylmethyl) indole according to the method of Example 59 gave 1-(2-cyclopropanecarbonylaminoethyl)-3-(1-imidazolylmethyl)indole, m.p. 136°–137° C. (from isopropanol/petrol (b.p. 60°–80° C.). Found: C, 69.55; H, 6.49; N, 18.23. $C_{18}H_{20}N_4O$ requires: C, 70.10; H, 6.54; N, 18.17%.

EXAMPLE 63

N-(2-Pyridyl)-N'-{2-[3-(imidazol-1-ylmethyl)indole-1-yl]ethyl}urea

A mixture of 1-(2-aminoethyl)-3-(1-imidazolylmethyl)indole (0.48 g) and N,N'-carbonyldiimidazole (0.325 g) was heated on a steam bath for 30 minutes. 2-Aminopyridine (0.19 g) was then added and the mixture was heated for a further 2 hours. It was then chromatographed on silica gel. Elution with chloroform and the chloroform/methanol (50:1) gave some impurity. Further elution with chloroform/methanol (50:1) gave pure product. The product containing fractions were evaporated and the residue was crystallised from ethyl acetate/petrol (b.p. 60°–80° C.) to give N-(2-pyridyl)-

N'-{2-[3-(imidazol-1-yl)ethyl]}urea (0.11 g), m.p. 198°–199° C. Found: C, 66.25; H, 5.72; N, 22.81. $C_{20}H_{20}N_6O$ requires: C, 66.65; H, 5.59; N, 23.32%.

EXAMPLE 64

1-[4-(2-Pyridylcarbamoyl)benzyl]-3-(1-imidazolylmethyl)indole

A mixture of 1-(4-carboxybenzyl)-3-(1-imidazolylmethyl) indole (1.50 g) and N,N'-carbonyldiimidazole (0.97 g) was heated under reflux in dioxan (10 ml) for 1 hour to give a clear solution. 2-Aminopyridine (0.94 g) was added and the solution was heated under reflux for a further 1.5 hours and then evaporated. The residue was dissolved in ethyl acetate and the solution was washed well with water and dried ($Na_2SO_4$). Evaporation of the solvent gave an oil which crystallised on trituration with ether. The solid was crystallised from isopropanol to give 1-[4-(4-pyridylcarbamoyl)benzyl]-3-(1-imidazolylmethyl)indole (0.45 g), m.p. 191°–193° C. Found: C, 73.22; H, 5.44; N, 16.86. $C_{25}H_{21}N_5O$ requires: C, 73.69; H, 5.18; N, 17.19%.

EXAMPLE 65

1-[4-(2-Thiazolylcarbamoyl)benzyl]-3-(1-imidazolylmethyl)indole

Successive treatment of 1-(4-carboxybenzyl)-3-(1-imidazolylmethyl)indole with N,N'-carbonyldiimidazole and 2-aminothiazole according to the method of Example 64 gave 1-[4-(2-thiazolylcarbamoyl)benzyl]-3-(1-imidazolylmethyl)indole, m.p. 197°–199° C. (from acetone/$H_2O$). Found: C, 64.02; H, 4.58; N, 16.50. $C_{23}H_{19}N_5OS.H_2O$ requires: C, 64.03; H, 4.91; N, 16.24%.

EXAMPLE 66

1-[4-(2-Pyrimidinylcarbamoyl)benzoyl]-3-(1-imidazolylmethyl)indole

Successive treatment of 1-(4-carboxybenzyl)-3-(1-imidazolylmethyl)indole with N,N'-carbonyldiimidazole and 2-aminopyrimidine according to the method of Example 64 gave 1-[4-(2-pyrimidinylcarbamoyl) benzyl]-3-(1-imidazolylmethyl)indole, m.p. 194°–197° C. (from ethanol/ether). Found: C, 69.02; H, 4.96; N, 20.07. $C_{24}H_{20}N_6O.\frac{1}{2}H_2O$ requires: C, 69.04; H, 5.07; N, 20.13%.

EXAMPLE 67

5-Bromo-1-[2-(2-Pyridylcarbamoyl)ethyl]-3-(1-imidazolylmethyl)indole

Successive treatment of 5-bromo-1-(2-carboxyethyl)-3-(1-imidazolylmethyl)indole with N,N'-carbonyldiimidazole and 2-aminopyridine according to the method of Example 64 gave 5-bromo-1-[2-(2-pyridylcarbamoyl)ethyl]-3-(1-imidazolylmethyl)indole, m.p. 165°–167° C. (from isopropanol/petrol (b.p. 60°–80° C.). Found: C, 56.67; H, 4.46; N, 16.87. $C_{20}H_{18}BrN_5O$ requires: C, 56.61; H, 4.28; N, 16.51%.

EXAMPLE 68

5-Bromo-1-[2-(N-methanesulphonylcarbamoyl)ethyl]-3-(1-imidazolylmethyl)indole

A mixture of 5-bromo-1-(2-carboxyethyl)-3-(1-imidazolylmethyl) indole (0.87 g) and N,N'-carbonyldiimidazole (0.51 g) was heated on a steam bath for 1.5 hours to give a clear melt. Methanesulphonamide (0.47 g) was added and the mixture was heated at 120° C. for 2 hours and then cooled and dissolved in a small volume of ethanol. Some insoluble material was filtered off and the filtrate was evaporated and the residue was chromatographed on silica gel. Elution with chloroform gave initially some impurity. Further elution with a mixture of chloroform and methanol (9:1) gave a mixture of product and imidazole. The product containing fractions were evaporated and the residue was crystallised from a mixture of methanol and ether to give 5-bromo-1-[2-(N-methanesulphonylcarbamoyl)ethyl]-3-(1-imidazolylmethyl)indole (0.31 g,), m.p. 199°–201° C. Found: C, 45.21; H, 4.18; N, 12.95. $C_{16}H_{17}BrN_4O_3S$ requires: C, 45.18; H, 4.03; N, 13.17%.

EXAMPLE 69

1-[4-(N-Benzoylcarbamoyl)benzyl]-3-(1-imidazolylmethyl)indole

A mixture of 1-(4-carboxy benzyl)-3-(1-imidazolylmethyl) indole (1.50 g) and N,N'-carbonyldiimidazole (0.97 g) were heated at 120° C. for 2 hours and then benzamide (1.21 g) was added. The mixture was heated at 120° C. for a further 2 hours and then cooled. The residue was partitioned between water and ethyl acetate. The aqueous layer was separated and the organic layer was dried ($Na_2SO_4$). Evaporation of the solvent gave a gum which was chromatographed on silica gel. Elution with chloroform gave initially some impurity, pure product was eluted with a mixture of chloroform and methanol (50:1). Evaporation of the product-containing fractions gave a solid which was crystallised from ethanol to give 1-[4-(N-benzoylcarbamoyl)benzyl]-3-(1-imidazolylmethylindole (0.57 g), m.p. 201.5°–202.5° C. Found: C, 74.18; H, 5.25; N, 12.78. $C_{27}H_{22}N_4O_2$ requires: C, 74.63; H, 5.11; N, 12.90%.

EXAMPLE 70

1-[4-(N-Acetylcarbamoyl)benzyl]-3-(1-imidazolylmethyl)indole

Successive treatment of 1-(4-carboxybenzyl)-3-(1-imidazolylmethyl)indole with N,N'-carbonyldiimidazole and acetamide according to the method of Example 69 gave 1-[4-(N-acetylcarbamoyl)benzyl]-3-(1-imidazolylmethyl)indole, m.p. 185.5°–186.5° C. (from ethyl acetate/ether). Found: C, 70.47; H, 5.44; N, 14.86. $C_{21}H_{20}N_4O_2$ requires: C, 70.95; H, 5.41; N, 15.05%.

EXAMPLE 71

1-[2-(N-Benzoylcarbamoyl)ethyl]-5-bromo-3-(1-imidazolylmethyl)indole

Successive treatment of 5-bromo-1-(2-carboxyethyl)-3-(1-imidazolylmethyl)indole with N,N'-carbonyldiimidazole and benzamide according to the method of Example 69 gave 1-[2-(N-benzoylcarbamoyl)ethyl]5-bromo-3-(1-imidazolylmethyl)indole, m.p. 124°–126° C. (from ethanol/ether). Found: C, 58.16; H, 4.26; N, 12.22. $C_{22}H_{19}BrN_4O_2$ requires: C, 58.54; H, 4.24; N, 12.42%.

EXAMPLE 72

1-[2-(5-Ethoxycarbonyl)thienylmethyl]-3-(1-imidazolylmethyl)indole hemifumarate

This compound was prepared as described in Example 4 using ethyl 5-bromomethylthenoate instead of α-bromo-p-tolunitrile. The hemifumarate salt had b.p. 119°–121° C. (from water). Found: C, 62.41; H, 5.10; N, 9.91. $C_{20}H_{19}N_3O_2S \cdot 0.5C_4H_4O_4$ requires: C, 62.40; H, 5.00; N, 9.92%.

EXAMPLE 73

1-[2-(5-Methoxycarbonyl)furanylmethyl]-3-(1-imidazolylmethyl)indole

This compound was prepared as described in Example 4 using methyl 5-chloromethylfuroate instead of α-bromo-p-tolunitrile. The product had m.p. 97°–99° C. (from toluene/petrol (b.p. 60°–80° C.)). Found: C, 67.97; H, 5.04; N, 12.15. $C_{19}H_{17}N_3O_3$ requires: C, 68.05; H, 5.11; N, 12.53%.

EXAMPLE 74

1-[2-(5-Carboxy)thienylmethyl]-3-(1-imidazolylmethyl)indole

This compound was prepared from 1-[2-(5-ethoxycarbonyl) thienylmethyl]-3-(1-imidazolylmethyl)indole by the method of Example 24. The crude product was dissolved in a slight excess of 2 N sodium hydroxide filtered and the product precipitated by the addition of acetic acid, m.p. 228°–229° C. Found: C, 63.87; H, 4.47; N, 12.21. $C_{18}H_{15}N_3O_2S$ requires: C, 64.09; H, 4.48; N, 12.46%.

EXAMPLE 75

1-Carbamoylethyl-3-(1-imidazolylmethyl)indole (1 g) was added to distilled water (900 ml) and the pH adjusted to 5 with hydrochloric acid. Sodium chloride (18 g) was added and the solution made up to 2 liters. The final solution was sterilised by filtration through a bacteria-proof filter under aseptic conditions into 10 ml glass vials so as to comply with the test for sterility of Appendix 121 British Pharmacopea 1973.

EXAMPLE 76

Capsules are compounded from the following ingredients:

|  | mg/capsule |
|---|---|
| 1-Carbamoylethyl-3-(1-imidazolylmethyl)indole | 20 |
| Lactose | 250 |
| Maize starch | 75 |
| Magnesium stearate | 5 |
|  | 350 mg |

The ingredients are thoroughly blended, granulated and then filled into hard gelatine capsules of the desired size.

We claim:

1. A compound of the formula

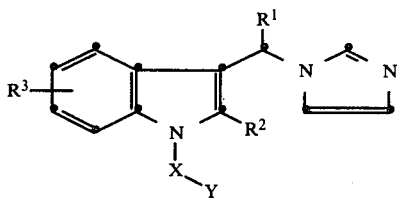

(I)

wherein $R^1$ is hydrogen or $C_1$–$C_4$ lower alkyl; $R^2$ is hydrogen, $C_1$–$C_6$ alkyl, $C_3$–$C_6$ cycloalkyl, phenyl, or phenyl monosubstituted with $C_1$–$C_4$ lower alkyl, $C_1$–$C_4$ lower alkoxy, fluorine, chlorine or bromine; $R^3$ is hydrogen, $C_1$–$C_4$ lower alkyl, $C_1$–$C_4$ alkoxy, hydroxy, trifluoromethyl, di($C_1$–$C_4$ lower alkyl)amino, fluorine, chlorine or bromine; X is

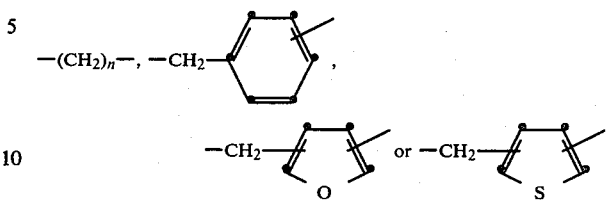

wherein n is an interger of from 1 to 3; Y is $CO_2R^4$, $CONHR^5$, $CON(C_1$–$C_4$ lower alkyl$)_2$, CN, 5-tetrazolyl, $CONHCOR^6$, CONHCN or $CONHSO_2R^6$; or, when X is $(CH_2)_n$ and n is 2 or 3, Y is $NH_2$, $NHCOR^6$, $NHCO_2(C_1$–$C_4$ lower alkyl), $NHCONHR^5$, $NHSO_2R^6$,

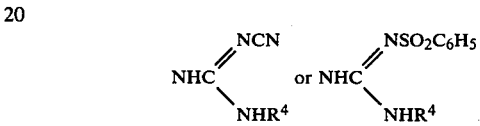

$R^4$ is hydrogen or $C_1$–$C_4$ lower alkyl; $R^5$ is hydrogen, $C_1$–$C_4$ lower alkyl, $C_3$–$C_6$ cycloalkyl, phenyl, 2-thiazolyl, 2-pyridyl, 2-pyrazinyl, 2-pyrimidinyl, or 2-pyridazinyl; $R^6$ is $C_1$–$C_4$ lower alkyl, $C_3$–$C_6$ cycloalkyl, 2-pyridyl, phenyl or phenyl monosubstituted with $C_1$–$C_4$ lower alkyl, $C_1$–$C_4$ lower alkoxy, fluorine, chlorine or bromine or a pharmaceutically acceptable acid addition salt thereof.

2. A compound of claim 1 wherein $R^1$, $R^2$ and $R^3$ are each hydrogen.

3. A compound of claim 1 or 2 wherein X is:

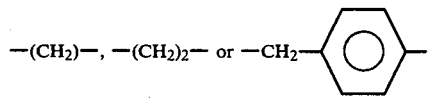

4. A compound of claim 1 or 2 wherein Y is $CO_2H$, $CO_2CH_2CH_3$, $CONH_2$, $CONHC_6H_5$, $NHSO_2C_6H_5$, $NHCONHCH_3$, $NHCONHC_6H_5$ $NHCOC_6H_5$ or tetrazolyl.

5. 1-carboxyethyl-3-(1-imidazolylmethyl)indole.

6. 1-carboxyethyl-2-cyclopropyl-3-(1-imidazolylmethyl)indole.

7. 1-(4-carboxybenzyl)-3-(1-imidazolylmethyl)indole.

8. 1-carboxymethyl-3-(1-imidazolylmethyl)indole.

9. 1-carbamoylethyl-3-(1-imidazolylmethyl)indole.

10. 1-(4-carbamoylbenzyl)-3-(1-imidazolylmethyl)indole.

11. 5-Bromo-1-carboxyethyl-3-(1-imidazolylmethyl)indole.

12. A pharmaceutical composition useful in inhibiting the action of thromboxane synthetase enzyme in an animal comprising an effective amount of a compound of claim 1 and a pharmaceutically acceptable carrier.

13. A pharmaceutical composition of claim 12 wherein said compound is 1-carboxyethyl-3-(1-imidazolylmethyl)indole.

14. A pharmaceutical composition of claim 12 wherein said compound is 1-carboxyethyl-2-cyclopropyl-3-(1-imidazolylmethyl)indole.

15. A pharmaceutical composition of claim 12 wherein said compound is 1-(4-carboxybenzyl)-3-(1-imidazolylmethyl)indole.

16. A pharmaceutical composition of claim 12 wherein said compound is 1-carboxymethyl-3-(1-imidazolylmethyl)indole.

17. A pharmaceutical composition of claim 12 wherein said compound is 1-carbamoylethyl-3-(1-imidazolylmethyl)indole.

18. A pharmaceutical composition of claim 12 wherein said compound is 1-(4-carbamoylbenzyl)-3-(1-imidazolylmethyl)indole.

19. A pharmaceutical composition of claim 12 wherein said compound is 5-bromo-1-carboxyethyl-3-(1-imidazolylmethyl)indole.

20. A method of inhibiting the action of thromboxane synthetase enzyme in an animal in need of treatment comprising administering to said animal an effective amount of a compound of claim 1.

21. A method of claim 20 wherein the compound is 1-carboxyethyl-3-(1-imidazolylmethyl)indole.

22. A method of claim 20 wherein the compound is 1-carboxyethyl-2-cyclopropyl-3-(1-imidazolylmethyl)indole.

23. A method of claim 20 wherein the compound is 1-(4-carboxybenzyl)-3-(1-imidazolylmethyl)indole.

24. A method of claim 20 wherein the compound is 1-carboxymethyl-3-(1-imidazolylmethyl)indole.

25. A method of claim 20 wherein the compound is 1-carbamoylethyl-3-(1-imidazolylmethyl)indole.

26. A method of claim 20 wherein the compound is 1-(4-carbamoylbenzyl)-3-(1-imidazolylmethyl)indole.

27. A method of claim 20 wherein the compound is 5-bromo-1-carboxyethyl-3-(1-imidazolylmethyl)indole.

* * * * *